United States Patent [19]

Fechtig et al.

[11] 3,996,208

[45] Dec. 7, 1976

[54] 6-ACYLAMINO-PENAM-3-CARBOXYLIC ACIDS

[75] Inventors: Bruno Fechtig, Reinach; Karoly Kocsis, Basel; Hans Bikel, Binningen, all of Switzerland

[73] Assignee: Ciba-Geigy Corporation, Ardsley, N.Y.

[22] Filed: Mar. 21, 1973

[21] Appl. No.: 344,020

[30] Foreign Application Priority Data

Mar. 22, 1972 Switzerland ............... 4251/72
Sept. 1, 1972 Switzerland ............... 12919/72
Dec. 20, 1972 Switzerland ............... 18530/72

[52] U.S. Cl. .................. 260/239.1; 260/243 C; 424/246; 424/271
[51] Int. Cl.[2] ......................... C07D 499/46
[58] Field of Search ................. 260/239.1

[56] References Cited

UNITED STATES PATENTS

| 3,481,922 | 12/1969 | Holdrege | 260/239.1 |
| 3,483,188 | 12/1969 | McGregor | 260/239.1 |
| 3,579,501 | 5/1971 | McGregor | 260/239.1 |

FOREIGN PATENTS OR APPLICATIONS

| 505,144 | 5/1971 | Switzerland |
| 1,162,261 | 8/1969 | United Kingdom |

*Primary Examiner*—Paul M. Coughlan, Jr.
*Attorney, Agent, or Firm*—Joseph G. Kolodny; John J. Maitner; Theodore O. Groeger

[57] ABSTRACT

6-acylamino-penam-3-carboxylic acids and 7-acylamino-3-cephem-4-carboxylic acids in which the acyl group has the formula

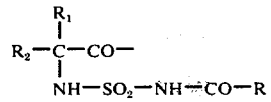

in which $R_1$ is hydrogen, $R_2$ is optionally substituted phenyl, thienyl or furyl or $R_1$ and $R_2$ together are optionally substituted cycloalkyl, and R is a radical which is linked through a carbon, oxygen, sulphur or nitrogen atom.

12 Claims, No Drawings

6-ACYLAMINO-PENAM-3-CARBOXYLIC ACIDS

The invention relates to new therapeutically valuable derivatives of 6-amino-2,2-dimethyl-penam-3-carboxylic acid and of 7-amino-ceph-3-em-4-carboxylic acid and their salts, processes for their manufacture and pharmaceutical preparations which contain the new compounds.

The new compounds have the general formula I

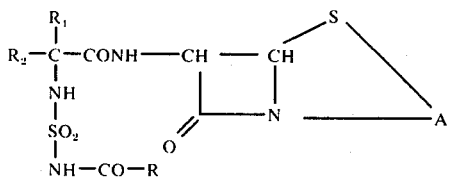

wherein the grouping —S—A— represents a radical of the formula Ia or Ib

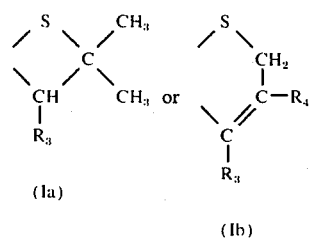

wherein $R_3$ denotes an optionally protected carboxyl group and $R_4$ represents hydrogen or an optionally substituted methyl group and wherein, if the radicals $R_1$ and $R_2$ are separate, $R_1$ is hydrogen and $R_2$ is optionally substituted phenyl, thienyl or furyl, and if the radicals $R_1$ and $R_2$ are linked, they form, together with the carbon atom, an optionally substituted cycloalkyl ring of 4 to 7 carbon atoms, and wherein R represents hydrogen or a radical with, preferably, at most 20, above all maximally 10, carbon atoms which is bonded by means of a carbon, oxygen, sulphur or nitrogen atom.

Substituents of the abovementioned cyclic radicals $R_2$ or $R_1 + R_2$ are, for example, lower alkyl such as methyl, lower alkoxy such as methoxy, halogen atoms, for example fluorine, chlorine and trifluoromethyl, the nitro group and above all carbamoyl and acyl, especially lower alkanoyl such as acetyl, acylamino, especially lower alkanoylamino and lower alkoxycarbonylamino, for example acetylamino, tert.butoxycarbonylamino, di-lower-alkylamino, for example dimethylamino, lower alkanoyloxy such as acetoxy and lower alkoxycarbonyl such as methoxycarbonyl. The cyclic radicals are preferably unsubstituted. $R_1 + R_2$ together with the carbon atom represent above all cyclopentyl or cyclohexyl. If $R_2$ represents thienyl or furyl, these radicals are bonded in the 2- or 3-position, preferably in the 2-position.

Above all, $R_1$ represents hydrogen and $R_2$ represents unsubstituted phenyl.

As mentioned, R denotes hydrogen or a radical bonded via oxygen, sulphur or nitrogen, but preferably via carbon or nitrogen.

A radical bonded via a carbon atom (hereafter referred to as $R_a$) is an optionally substituted aliphatic, cycloaliphatic, cycloaliphatic-aliphatic, aromatic or araliphatic hydrocarbon radical or a heterocyclic or heterocyclylaliphatic radical or a substituted formyl radical.

An aliphatic hydrocarbon radical $R_a$ is above all a lower alkyl radical with 1–5 carbon atoms such as methyl, ethyl, propyl, isopropyl, n-butyl and tert.butyl. Such a radical can optionally be substituted by one or more substituents.

As substituents there should be mentioned free, esterified or etherified hydroxyl or mercapto groups, such as halogen, especially chlorine or fluorine, or lower alkanoyloxy such as acetoxy, lower alkoxy such as methoxy, aryloxy, such as phenoxy which is optionally substituted, especially by halogen, nitro, lower alkyl or lower alkoxy, for example p-chlorophenoxy, lower alkylmercapto such as methylmercapto, and also trifluoromethyl, free or functionally modified carboxyl groups, for example ester groups, especially lower alkoxycarbonyl such as methoxycarbonyl, ethoxycarbonyl, nitrile, optionally substituted carbamoyl, for example N-lower alkylcarbamoyl such as N-methyl-carbamoyl or N-halogeno-lower alkylcarbamoyl such as β-chloroethylcarbamoyl, optionally substituted amino groups such as mono- or di-lower alkylamino, for example dimethylamino, or acylamino, especially lower alkanoylamino, for example acetylamino, or sulphonylamino, for example methylsulphonylamino, the nitro group and acyl groups, especially acyl groups of carboxylic acids, for example lower alkanoyl, such as acetyl, or monocyclic aroyl, such as benzoyl.

A cycloaliphatic hydrocarbon radical $R_a$ is, for example, a cycloalkyl or cycloalkenyl radical with 3–8, preferably 5–6, carbon atoms, for example cyclohexyl and cyclohexenyl, a cycloaliphatic-aliphatic hydrocarbon radical is, for example, a cycloalkyl- or cycloalkenyl-lower alkyl radical, wherein cycloalkyl, cycloalkenyl and lower alkyl have the meanings mentioned, for example cyclopentylmethyl and cyclohexenylmethyl. These radicals can be substituted in the same manner as the aliphatic hydrocarbon radicals described above; they can also possess lower alkyl groups as substituents.

An aromatic radical $R_a$ is a monocyclic or bicyclic radical, for example phenyl and preferably naphthyl. These radicals can be substituted in the same manner as the cyclic aliphatic radicals. Examples which should be mentioned are p-nitrophenyl, m-methoxyphenyl, m-carboxylphenyl, dicarboxyphenyl, methylsulphonylaminophenyl and above all α- and β-naphthyl.

Araliphatic radicals $R_a$ can also be monocyclic or bicyclic. Above all, they are phenyl-lower alkyl radicals such as benzyl or phenylethyl. These radicals can also carry the substituents indicated above for the aliphatic cyclic radicals.

Heterocyclic radicals $R_a$ are monocyclic or bicyclic radicals which contain nitrogen, sulphur and/or oxygen as hetero-atoms. They possess 5–8, preferably 5–6, ring members per ring. They can be saturated or unsaturated. Preferably, they are of aromatic character. They possess 1–4, preferably 1–2, hetero-atoms, above all one hetero-atom. They can possess a fused benzene ring. As examples there should be mentioned: Furyl, thienyl, pyrryl, indolyl, oxazolyl, thiazolyl, imidazolyl, pyrazolyl, triazolyl, tetrazolyl, thiadiazolyl, thiazolidinyl, tetrahydrofuranyl, pyrrolidyl, pyridyl, quinolyl, isoquinolyl, tetrahydropyranyl, pyrimidyl, pyridazinyl, pyrazinyl, triazinyl, tetrazinyl, piperidyl, morpholinyl and thiamorpholinyl. The rings can possess substituents, as indicated above for the cycloaliphatic rings.

Heterocyclic-aliphatic radicals $R_a$ are above all heterocyclic-lower alkyl radicals, for example heterocyclylmethyl radicals. Therein, the heterocyclyl radical is a radical such as described above. These radicals can also carry the substituents indicated above for cycloaliphatic radicals.

A substituted formyl radical is above all the carbamoyl group, also a lower alkanoyl radical such as the acetyl radical, or a monocyclic aroyl radical, such as an optionally substituted benzoyl radical. Substituents of the aromatic radical are those mentioned above.

A radical R bonded by an oxygen atom or sulphur atom (hereafter referred to as $R_b$) is, for example, an optionally substituted aliphatic, cycloaliphatic, araliphatic or aromatic hydrocarbon radical bonded via an oxygen atom or a sulphur atom. The hydrocarbon radical has the same meaning as explained above for $R_a$; the substituents are also the same as indicated above for $R_a$.

A radical bonded via a nitrogen atom (hereafter referred to as $R_c$) is an unsubstituted or substituted amino group. The amino group can possess two substituents but preferably has one substituent. Substituents of the amino group are optionally substituted aliphatic, cycloaliphatic, cycloaliphatic-aliphatic, aromatic or araliphatic hydrocarbon radicals or heterocyclic or heterocyclyl-aliphatic radicals such as defined above as $R_a$, above all a monoazacyclic or diazacyclic radical of aromatic character. The amino group can also be substituted by a radical bonded via an oxygen atom, as indicated above for $R_b$, as well as by an OH group, an $NH_2$ group optionally substituted by a radical $R_a$, a CN group or an acyl group, wherein acyl can be derived from a monocarboxylic acid or dicarboxylic acid or above all from a sulphonic acid. Monocarboxylic acids and dicarboxylic acids are above all those with up to 10 carbon atoms, for example phthalic acid, maleic acid, malonic acid and lower alkanoic acids such as acetic acid, propionic acid and butyric acid. Sulphonic acids are especially monocyclic or bicyclic aromatic sulphonic acids and also aliphatic sulphonic acids, such as benzenesulphonic acid, toluenesulphonic acids, naphthalenesulphonic acids, methanesulphonic acid and ethanesulphonic acid. The acids can be substituted by the substituents indicated for $R_a$. A heterocyclyl radical which substitutes the amino group can also be bonded via a ring nitrogen atom to the amino group and can, for example, be a thiazol-3-yl or rhodanin-3-yl radical. The amino group can also, together with the substituent, form a guanidino, alkyleneimino, oxaalkyleneimino, thiaalkyleneimino or azaalkyleneimino group, for example a piperidino, morpholino, thiamorpholino or piperazino group. In the cyclic radicals mentioned, "alkylene" denotes a $(CH_2)_n$ group, wherein $n$ represents 2–7, preferably 4–5. These groups can be substituted, especially by lower alkyl groups, for example methyl.

The substituent $R_3$ present in the penicillanic acid and cephalosporanic acid derivatives of the formula Ia and Ib is, as has been mentioned, a free or protected carboxyl group. By a protected carboxyl group there is here to be understood a functionally modified carboxyl group, such as an esterified or amidised carboxyl group, or a carboxyl group present in the anhydride form.

An esterified carboxyl group $R_3$ is preferably a group which can be split easily, for example a group which can be split to the free carboxyl group, if appropriate in an acid or weakly alkaline medium, solvolytically, for example by hydrolysis or alcoholysis, hydrogenolytically, reductively, by nucleophilic exchange, photolytically or enzymatically.

Ester groups which can easily be split by solvolysis with a solvent containing hydroxyl groups, for example water or alcohols, such as, for example, methanol or ethanol, preferably under neutral conditions, are above all those which are derived from silyl, germanyl, plumbyl or stannyl alcohol. Such groups are described, for example, in British patent specification No. 1,073,530, in Netherlands published specification No. 67/17,107 and in German Offenlegungsschrift No. 1,800,698. In particular, groups of the formula $R_5R_6R_7$ Si—OCO— or $R_5R_6R_7$Sn—OCO— can be used, wherein $R_5$, $R_6$ and $R_7$ are identical or different and represent alkyl, especially lower alkyl, aryl, for example phenyl, or aralkyl, such as phenyl-lower alkyl, such as benzyl.

Esters which are easily split in an acid medium, for example in the presence of hydrogen chloride, hydrogen fluoride or hydrogen bromide, or of organic acids such as acetic acid, trifluoroacetic acid, formic acid or their mixtures with water, are above all those which are derived from lower alkanols which are poly-branched in the α-position or lower alkanols which contain, in the α-position, one or more electron donors such as optionally substituted aromatic hydrocarbon radicals or heterocyclyl radicals of aromatic character such as phenyl, furyl, thienyl or aroyl radicals, such as benzoyl, or acyloxy radicals, such as aroyloxy or lower alkanoyloxy. Such ester groups are, for example, tert, butoxycarbonyl, tert. amyloxycarbonyl, cyclopentyloxycarbonyl, cyclohexyloxycarbonyl, adamantyloxycarbonyl, furfuryloxycarbonyl, 2-tetrahydrofuryloxycarbonyl, 2-tetrahydropyranyloxycarbonyl, benzyloxycarbonyl, p-nitrobenzyloxycarbonyl, p-methoxy-benzyloxycarbonyl, α-methyl-α-diphenylyl-methyloxycarbonyl, 3,4-dimethoxybenzyloxycarbonyl, 3,5-dimethoxybenzyloxycarbonyl, diphenylmethyloxycarbonyl, di(p-methoxyphenyl)-methyloxy-carbonyl, triphenylmethyloxycarbonyl, benzoylmethoxycarbonyl, benzoyloxymethyloxycarbonyl, acetoxymethylcarbonyl and pivaloyloxymethyloxycarbonyl.

Ester groups which can be split hydrolytically under weakly basic or acid conditions are, for example, activated esters which are derived from optionally substituted phenol or benzyl alcohol, such as 4-nitrophenyl, 2,4-dinitrophenyl, 4-nitrobenzyl, 2,4,6-trichlorophenyl, and 2,3,4,5,6-pentachlorophenyl esters, and also, for example, phthaliminomethyl, succiniminomethyl, triphenylmethyl and bis-(4-methoxyphenyloxy)methyl esters.

Examples of ester groups which can be split by hydrogenolysis are ester groups derived from optionally substituted benzyl alcohol, for example p-nitrobenzyl alcohol. Ester groups which can be split by reduction without the conjoint action of catalysts, for example by treatment with nascent hydrogen, or by electrolytic reduction, are of major importance. Such groups are derived, above all, from 2-halogeno-lower alkanols, for example 2,2,2-trichloroethanol, 2-chloroethanol, 2-bromoethanol and 2-iodoethanol and also, for example, from benzoylmethanol or 4-pyridylmethanol. These alcohol groups can be removed by treatment with chemical reducing agents, preferably under neutral or weakly acid conditions, for example with zinc in the presence of aqueous acetic acid or formic acid or zinc in a lower alkanol or in pyridine, or by chromium- (II) reagents. The 4-pyridylmethyloxy group is appropriately removed by electrolytic reduction.

Ester groups which can be easily split off photolytically, especially by irradiation with ultra violet light, preferably under neutral or acid conditions, are derived from methanols which contain one or two aryl radicals which are substituted, for example, by lower alkoxy groups, especially methoxy, and/or nitro groups. Such groups are above all 3-methoxy- and 4-methoxy-benzyloxycarbonyl, 3,4-dimethoxy- and 3,5-dimethoxybenzyloxycarbonyl, 2-nitrobenzyloxycarbonyl, 4,5-dimethoxy-2-nitro-benzyloxycarbonyl, α-phenyl-α-(3,4-dimethoxy-6-nitro-phenyl)-methyloxycarbonyl and α-methyl-α-(3,4-dimethoxy-6-nitrophenyl)-methyloxycarbonyl.

Esters which can be split enzymatically are above all those which contain an ester group which can be split under physiological conditions. These esters can readily be resorbed in the organism and can therefore, as such, be used therapeutically. Esters of this nature are described, for example, in British patent specification No. 1,229,453 and in German Patent Application DT No. 1,951,012. The esters are derived from alcohols of the formula $HO-CH_2OCO-R''_3$, wherein $R''_3$ can represent a hydrogen atom, an alkyl radical, a cycloalkyl radical, a cycloalkylalkyl radical, an aryl radical, an aralkyl radical or a heterocyclyl radical. In particular, $R''_3$ can represent a lower alkyl radical with at most 5 carbon atoms, such as methyl, ethyl, propyl, isopropyl butyl and isobutyl, above all tert.-butyl, and also a monocyclic cycloalkyl radical with 3 to 7 carbon atoms; a bicyclic cycloalkyl radical, such as a 1-bicyclo-(2,2,2)octyl or adamantyl radical; a monocyclic aryl radical, for example an optionally substituted phenyl radical; a bicyclic aryl radical, such as a 1-naphthyl, a 2-naphthyl or a substituted naphthyl radical; a monocyclic or bicyclic aralkyl radical, for example a benzyl or phenylethyl radical or a naphthyl-lower alkyl radical, such as naphthylmethyl. $R''_3$ can also represent a heterocyclyl radical with 5–6 ring carbon atoms and at least one nitrogen, sulphur or oxygen atoms, for example thienyl, furyl, pyrryl, oxazolyl, thiazolyl and imidazolyl.

Examples of substituents in the above ring systems which form a part of $R''_3$ are, inter alia, lower alkyl radicals, lower alkoxy radicals, lower alkylmercapto radicals, lower halogenoalkyl radicals, such as mono-, di- or tri-halogenoalkyl radicals, in which the halogen can be fluorine, chlorine or bromine, as well as nitro groups. Processes for the manufacture of the above esters are described in the British Patent Specification and German Application which have been mentioned.

The carboxyl group $R_3$ can also be esterified by a lower alkanol, such as methanol or ethanol.

In the amidised carboxyl group $R_3$ the amide nitrogen atom can optionally be substituted, for example, by monovalent or bivalent aliphatic hydrocarbon radicals, which can optionally be interrupted by oxygen, nitrogen or sulphur atoms. Such radicals are above all lower alkyl, for example as mentioned above, especially methyl, or lower alkylene, for example 1,4-butylene or 1,5-pentylene, oxa-lower alkylene, for example 3-oxa-1,5-pentylene, or aza-lower alkylene, for example 3-methyl-3-aza-1,5-pentylene.

A protected carboxyl group $R_3$ present in the form of an anhydride, preferably in the form of a mixed anhydride, is above all a group which can be split hydrolytically. The second acyl radical is, for example, the acyl radical of a carboxylic acid, especially of a lower alkanoic acid which is optionally substituted, for example by halogen, for example acetyl, trichloroacetyl or pivaloyl, or the acyl radical of a carbonic acid monoester, especially a mono-lower alkyl ester, for example ethoxycarbonyl or isobutoxycarbonyl.

The radical $R_4$ in the cephalosporanic acid derivatives of the formula Ib represents, as mentioned, a hydrogen atom, wherein the side chain in the 3-position of Cephalosporin C is missing) or an unsubstituted or substituted methyl group. Substituents of the methyl group are above all a free, esterified or etherified hydroxyl group, an etherified mercapto group, an optionally N-substituted carbamoyloxy or thiocarbamoylmercapto group, a quaternary ammonium group or the nitrile group.

An esterified hydroxyl group contains, as the acid radical, above all the radical of a carboxylic acid or thiocarboxylic acid, for example lower alkanoyl which is optionally substituted by halogen atoms, especially chlorine, such as formyl, propionyl, butyryl, pivaloyl and chloroacetyl, but especially acetyl, or aroyl or aroyl-lower alkanoyl which are optionally substituted, for example by lower alkyl, lower alkoxy, halogen or nitro, for example benzoyl or phenylacetyl, and also, as a thiocarboxylic acid radical, especially aroylthio which is optionally substituted as mentioned, above all benzoylthio. Additionally, hydroxyl groups esterified by hydrogen halide acids should be mentioned; the methyl group $R_4$ can therefore be substituted, for example, by fluorine, chlorine or bromine.

Etherified hydroxyl groups are described, for example, in Belgian Pat. No. 719,710. Lower alkoxy, such as methoxy, ethoxy and n-propoxy, furanyl and pyranyl should be singled out.

Etherified mercapto groups for example contain, as etherifying radicals, lower alkyl, for example methyl, and also optionally substituted phenyl or heterocyclyl, wherein the substituents can be the same as indicated above for the aromatic and heterocyclic radicals $R_a$. The heterocyclyl radicals preferably have 5–6 ring atoms and contain, as hetero-atoms, nitrogen, optionally in the N-oxidised form, and/or oxygen or sulphur. Examples to be mentioned are 1-oxidised 2-pyridyl, pyrimidyl, pyridazinyl, pyrazinyl, imidazolyl, imidazolinyl and pyrinyl. Optionally substituted heterocyclyl radicals of aromatic character with 5 ring atoms, which contain at least 2 nitrogen atoms and furthermore an additional hetero-atom from the group of nitrogen, oxygen and sulphur should be singled out particularly. Preferred substituents are lower alkyl radicals with 1–5 carbon atoms such as methyl, ethyl, propyl, isopropyl, n-butyl, isobutyl and tert.butyl, lower alkoxy or lower alkylthio radicals with 1–5 carbon atoms, especially methylthio, cycloalkyl radicals such as cyclopentyl and cyclohexyl, or aryl radicals such as phenyl or substituted phenyl, for example phenyl substituted by one or more nitro groups or halogen atoms or lower alkyl or lower alkoxy groups, or unsubstituted or substituted thienyl, especially thienyl-(2) or thienyl substituted as indicated for phenyl, or optionally monosubstituted or disubstituted amino groups, for example acetylamino, tert.butoxycarbonylamino, tert.-amyloxycarbonylamino and sulphonylamino. As examples of the heterocyclyl radicals there should be mentioned: 1H-1,2,3-triazol-5-yl, 1,3,4-triazol-2-yl, 5-methyl-1,3,4-triazol-2-yl, 1H-1,2,4-triazol-5-yl, 1-phenyl-3-methyl-1H-1,2,4-triazol-5-yl, 4,5-dimethyl-4H-1,2,4-triazol- 3-yl, 4-phenyl-4H-1,2,4-triazol-3-yl, 1H-tetrazol-5-yl, 1-methyl-1H-tetrazol-5-yl, 1-ethyl-1H-tetrazol-5-yl, 1-n-propyl-1H-tetrazol-5-yl, 1-isopropyl-1H-tetrazol-5-yl, 1-n-butyl-1H-tetrazol-5-yl, 1-cyclopentyl-1H-tetrazol-5-yl, 1-phenyl-1H-tetrazol-5-yl, 1-p-chlorophenyl-1H-tetrazol-5-yl, 1,2,3-thiadiazol-5-yl, 1,3,4-thiadiazol-2-yl, 1,2,4-thiadiazol-3-yl, 1,2,4-thiadiazol-5-yl, 3-methyl-1,2,4-thiadiazol-5-yl, 2-methyl-1,3,4-thiadiazol-5-yl, 2-methylthio-1,3,4-thiadiazol-5-yl, 2-ethyl-1,3,4-thiadiazol-5-yl, 2-n-propyl-1,3,4-thiadiazol-5-yl, 2-isopropyl-1,3,4-thiadiazol-5-yl, 2-phenyl-1,3,4-thiadiazol-5-yl, 1,2,4-oxadiazol-5-yl, 1,2,3-oxadiazol-5-yl, 1,3,4-oxadiazol-5-yl, 2-methyl-1,3,4-oxadiazol-5-yl, 2-ethyl-1,3,4-oxadiazol-5-yl, 2-phenyl-1,3,4-oxadiazol-5-yl, 2-p-nitrophenyl-1,3,4-oxadiazol-5-yl, 2-[thienyl-(2)]-1,3,4-oxadiazol-5-yl and thiatriazol-5-yl.

An optionally N-substituted carbamoyloxy group or thiocarbamoylmercapto group is, for example, a group of the formula —O—CO—NH—$R_8$ or

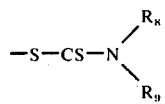

wherein $R_8$ is an optionally halogen-substituted lower alkyl radical and $R_9$ is hydrogen or $R_8$. Above all, $R_8$ is methyl, ethyl or chlorinesubstituted methyl or ethyl, especially β-chloroethyl.

In a quaternary ammonium-methyl group $R_4$ the ammonium part is preferably a pyridinium group which is optionally substituted, for example by lower alkyl, as mentioned above, or by optionally substituted carboxyl, such as lower alkoxycarbonyl, for example ethoxycarbonyl, or carbamoyl.

Salts of compounds of the present invention are above all pharmaceutically usable non-toxic salts of those compounds which can form salts with bases. Such salts are above all metal salts or ammonium salts, such as alkali metal salts, alkaline earth metal salts and earth metal salts, for example sodium, potassium, magnesium calcium or aluminium salts, as well as ammonium salts with ammonia or suitable organic amines, in which case it is possible to use for the salt formation above all aliphatic, cycloaliphatic, cycloaliphatic-aliphatic and araliphatic primary, secondary, or tertiary monoamines, diamines or polyamines, as well as heterocyclic bases, such as lower alkylamines, for example triethylamine, hydroxy-lower alkylamines, for example 2-hydroxyethylamine, bis-(2-hydroxyethyl)-amine or tri-(2-hydroxyethyl)-amine, basic aliphatic esters of carboxylic acids, for example 4-aminobenzoic acid 2-diethylaminoethyl ester, lower alkyleneamines, for example 1-ethyl-piperidine, cycloalkylamines, for example bicyclohexylamine or benzylamines, for example N,N'-dibenzyl ethylenediamine, and also bases of the pyridine type, for example pyridine, collidine or quinoline.

The new compounds can be in the form of mixtures of isomers, for example racemates, or of individual isomers, for example optically active antipodes.

The new compounds of the formula I display a pharmacological action, especially a particularly pronounced antibacterial action. Thus they are active against Gram-positive bacteria, such as Staphylococcus aureus, but above all against Gram-negative bacteria, for example Escheria coli, Klebsiella pneumonia, Salmonella typhosa and especially against Bacterium proteus a well as Pseudomonas aeruginosa. Thus they inhibit the growth of Pseudomonas aeruginosa at dilutions down to 0.4 γ/ml. They can therefore be used for combating infections which are caused by such microorganisms, and also as fodder additives, for the preservation of foodstuffs or as disinfectants.

Compounds to be singled out are 3-cephem compounds of the formula

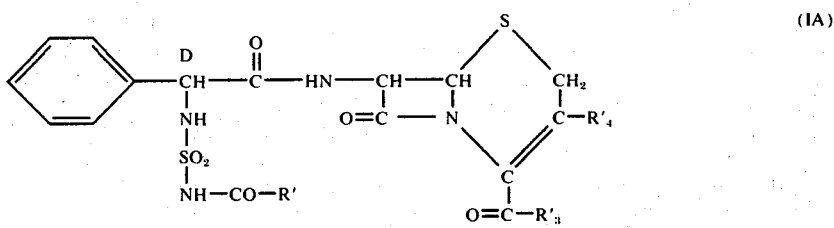

and especially penam compounds of the formula

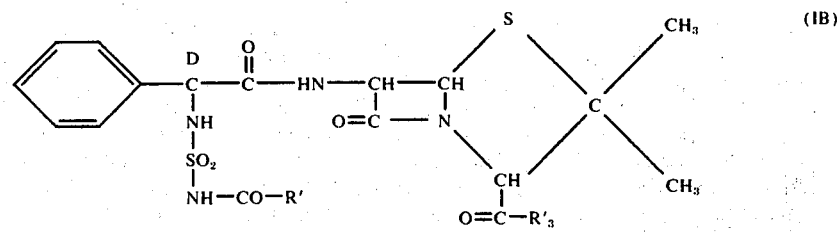

wherein $R'_3$ in particular is hydroxyl, lower alkoxy, for example methoxy or tert,-butoxy, 2-halogeno-lower alkoxy, for example 2,2,2-trichloroethoxy, 2-bromoethoxy or 2-iodoethoxy, phenacyloxy, phenyl-lower alkoxy, for example benzyloxy or diphenylmethoxy, amino, lower alkylamino, for example methylamino, di-lower alkylamino, for example dimethylamino, or morpholino, and $R'_4$ represents hydrogen, methyl, lower alkanoyloxymethyl, for example acetoxymethyl, pyridinium-methyl, 1-oxidised 2-pyridylthiomethyl, 1,3,4-thiadiazol-2-ylthiomethyl, 2-methyl-1,3,4-thiadiazol-5-ylthiomethyl, 3-methyl-1,2,4-thiadiazol-5-ylthiomethyl or 1-methyl-5-tetrazolylthiomethyl and wherein R' has the following meanings:

a. A lower alkyl radical which is optionally monosubstituted or disubstituted by lower alkoxy, for example methoxy or ethoxy, halogen, for example chlorine or fluorine, nitrile, esterified or amidised carboxyl, for example lower alkoxycarbonyl such as methoxycarbonyl or ethoxycarbonyl or carbamoyl or acyl, for example lower alkanoyl such as acetyl, above all methyl or methoxymethyl, or b. a phenyl or phenyl-lower alkyl radical which is optionally substituted by lower alkyl, for example methyl or ethyl, lower alkoxy, for example methoxy or ethoxy, halogen, for example chlorine or fluorine, esterified or amidised carboxyl, for example methoxycarbonyl, carbamoyl or optionally monosubstituted or disubstituted amino, for example di-lower alkylamino or lower alkanoylamino, for example acetylamino, for example p-acetylaminophenyl and p-dimethylaminophenyl, and especially a naphthyl radical, or c. an optionally substituted monocyclic azacyclic radical of aromatic character with 1–2 ring nitrogen atoms and 5–6 ring atoms, wherein the substituents are those mentioned under b) and additionally the hydroxyl group, above all pyridyl, especially pyridyl-(3), or pyrrole-(3), d. an optionally substituted monocyclic, monooxacyclic or monothiacyclic radical of aromatic character with 5–6 ring atoms, wherein the substituents are those mentioned under c), above all furyl-(2) or thienyl-(2), or e. an optionally substituted lower alkoxy, phenyloxy, lower alkylthio, for example methylthio or phenylthio radical which possesses halogen atoms, especially chlorine, or a di-lower alkylamino group, especially a dimethylamino group, as substituents, above all the methoxy radical, and f. an optionally substituted amino radical which possesses, as substituents, lower alkyl, for example methyl, or optionally substituted phenyl or an alkylene-(polymethylene) group which is interrupted by nitrogen, oxygen or sulphur and which, together with the amino group, forms a ring with 5–6 ring atoms, for example a morpholino group or especially a monoazacyclic or diazacyclic radical or aromatic character, such as a pyridyl, pyrimidyl or pyrazinyl radical. Possible substituents are those mentioned under (c). Above all, the amino group is substituted by an aromatic sulphonic acid.

Penam compounds of the formula IB, wherein R' represents a pyridyl or naphthyl radical which is unsubstituted or substituted as mentioned, or represents an aromatic sulphonylamino radical, and wherein R'$_3$ represents hydroxyl, as well as non-toxic salts, such as alkali metal salts, for example sodium or potassium salts, or alkaline earth metal salts, such as calcium salts, of these compounds, are therapeutically particularly valuable.

The new compounds are manufactured according to methods which are in themselves known. Thus they can be obtained if a. a compound of the formula II

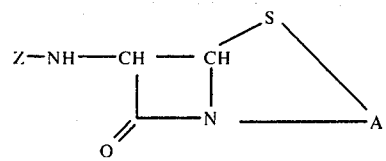

in which Z represents the radical

wherein $R_1$, $R_2$ and A have the meaning indicated for the formula I, is N-acylated with an acyl radical of the formula III $$-SO_2-NH-CO-R,$$

wherein R has the meaning indicated for the formula I, or b. a compound of the formula II, wherein Z represents hydrogen, is N-acylated with an acyl radical of the formula IV

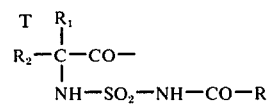

wherein R, $R_1$ and $R_2$ have the meaning indicated for the formula I and, if desired, in a resulting compound of the formula Ia or Ib an optionally functionally modified carboxyl group $R_3$ is converted into another $R_3$ group and/or an optionally substituted methyl group $R_4$ is converted into another $R_4$ group and/or, if desired, a compound obtained as the free acid is converted into a salt or a salt obtained is converted into the free acid and/or an isomer mixture obtained is separated into the individual isomers.

In a starting material of the formula II, the group $R_3$ in the radical —S—A— preferably denotes one of the abovementioned functionally modified, especially esterified, carboxyl groups, such as a carboxyl group esterified by di-lower alkylhalogenosilyl or tri-lower alkylsilyl or a carboxyl group esterified by phenyl-lower alkyl. A N-silylated or N-stannylated derivative of a starting material contains, for example, the abovementioned organic silyl or stannyl radicals, such as tri-lower alkylsilyl, for example trimethylsilyl, bonded to the amino group. Salts of starting compounds of the formula II are, in particular, those of compounds having a free carboxyl group, above all ammonium salts, such as tri-lower alkylammonium salts, for example triethylammonium salts, and also alkali metal salts.

The acylation of the compound II according to (a) or (b) with the acyl radical III and IV is carried out according to methods which are in themselves known, especially in the manner know from peptide chemistry for the acylation of weakly basic amino groups. The acylating agent used, which contains the acyl radical III or IV, is either the corresponding acid, in which case the reaction is carried out in the presence of a condensation agent, for example a carbodiimide such as dicyclohexylcarbodiimide, or in the presence of the Woodward reagent K or L, or a reactive acid derivative, for example an acid halide, especially a chloride or bromide, an acid azide, an activated ester or a mixed anhydride, for example an anhydride with a mono-esterified carbonic acid such as a carbonic acid lower alkyl ester, for example carbonic acid methyl ester, or with an optionally halogen-substituted lower alkanoic acid such as formic acid, pivalic acid or trichloroacetic acid. Above all, an acid halide, especially an acid chloride, is used for the acylation with the acyl radical $R_3$, and an activated ester, especially the p-nitrophenyl ester, 2,4-dinitrophenyl ester, 2,4,5- or 2,4,6-trichlorophenyl ester, pentachlorophenyl ester and also, for example, the cyanomethyl ester, N-hydroxysuccinimide ester, N-hydroxypiperidine ester and N-hydroxyphthalimide ester, is used for the acylation with the acyl radical IV.

The acylation reactions are carried out in the presence of a solvent or diluent, if desired in the presence of a catalyst and/or, if required, especially when using acid halides, in the presence of basic agents such as aliphatic, aromatic or heterocyclic nitrogen bases, for example triethylamine, diisopropylethylamine, N,N-diethylaminoacetic acid ethyl ester, N-ethylmorpholine, N,N-dimethylaniline, pyridine, p-dimethylaminopyridine, collidine or 2,6-lutidine.

The reaction is carried out at room temperature or with cooling or warming, for example at temperatures of $-70°$ to $100°$ C, if appropriate in an inert gas atmosphere, for example a nitrogen atmosphere, and/or with exclusion of moisture.

In a compound of the formula I obtained according to the invention, a protected carboxyl group $R_3$, especially an esterified carboxyl group which can easily be converted into the free carboxyl group, can be converted into the free carboxyl group in the manner indicated above. It is also possible, before splitting off the ester group, to convert the ester group into another ester group, for example to convert a 2-bromoethyl ester group into a 2-iodoethyl ester group.

In a compound of the formula I obtained in accordance with the process, or in a compound of the formula II used as the starting material, wherein $R_3$ represents a free carboxyl group, the latter can be converted in a manner which is in itself known into a protected carboxyl group, especially a functionally modified carboxyl group. Thus, a free carboxyl group can be esterified, for example by treatment with a diazo compound, such as diazo-lower alkane, for example diazomethane or diazoethane, or a phenyl-diazo-lower alkane, for example phenyldiazomethane or diphenyldiazomethane, or by reaction with an alcohol suitable for esterification in the presence of an esterifying agent, such as a carbodiimide, for example dicyclohexylcarbodiimide as well as carbonyldiimidazole, or in accordance with any other known and suitable esterification process, such as the reaction of a salt of the acid with a reactive ester of an alcohol with a strong inorganic acid or with a strong organic sulphonic acid. Furthermore, acid halides, such as acid chlorides, (manufactured, for example, by treatment with oxalyl chloride), activated esters (formed, for example, with N-hydroxy-nitrogen compounds) or mixed anhydrides (obtained, for example, with halogenoformic acid lower alkyl esters, such as chloroformic acid ethyl ester, or with halogenoacetic acid halides, such as trichloroacetic acid chloride) can be converted into an esterified carboxyl group by reaction with alcohols, optionally in the presence of a base, such as pyridine, and furthermore a mixed anhydride with a carbonic acid half-ester can be converted into an esterified carboxyl group by splitting off carbon dioxide.

Carboxyl groups esterified by organic silyl or stannyl groups can be formed in a manner which is in itself known, for example by treating compounds of the formula I or II, wherein $R_3$ represents a free carboxyl group, or salts, such as alkali metal salts, for example sodium salts, thereof, with a suitable silylating agent, such as a di-lower alkyl-dihalogenosilane, for example, dimethyldichlorosilane, a tri-lower alkyl-silyl halide, for example trimethyl-silyl chloride, or an optionally N-mono-lower alkylated, N,N-di-lower alkylated, N-tri-lower alkylsilylated or N-lower alkyl-N-tri-lower alkyl-silylated N-(tri-lower alkyl-silyl)-amine (see, for example, British Pat. No. 1,073,530) or with a suitable stannylating agent, such as a bis-(tri-lower alkyl-tin) oxide, for example bis-(tri-n-butyl-tin) oxide, a tri-lower alkyl-tin hydroxide, for example triethyl-tin hydroxide, a tri-lower alkyl-lower alkoxy-tin compounds, tetra-lower alkoxy-tin compound or tetra-lower alkyl-tin compound, or a tri-lower alkyl-tin halide, for example tri-n-butyl-tin chloride (see, for example, Netherlands published specification No. 67/17,107).

Mixed anhydrides of compounds of the formula I or II, wherein $R_3$ represents a free carboxyl group, can be manufactured by reacting such a compound, or preferably a salt thereof, especially an alkali metal or ammonium salt thereof, with a reactive derivative, such as a halide, for example the chloride, of an acid, for example a halogenoformic acid lower alkyl ester or a lower alkanecarboxylic acid chloride.

A resulting compound of the formula I, wherein the group $R_3$ represents a free carboxyl group, can be converted into the corresponding amide in a manner which is in itself known. Thus, for example, it is possible to treat the acid or a corresponding acid halide or mixed anhydride or a corresponding ester, especially an activated ester, but also, for example, a lower alkyl ester, such as the methyl ester or ethyl ester, with ammonia or a primary or secondary amine, and when using the acid a suitable condensation agent, such as a carbodiimide, for example dicyclohexylcarbodiimide, is used. It is also possible to react the free carboxylic acid with an isocyanate which is derived from the corresponding amine and to convert the mixed anhydride formed into the desired amide, whilst splitting off carbon dioxide.

In compounds of the formula I, wherein the fragment —S—A— represents the group of the formula Ib, a radical $R_4$ can be converted into another group of this nature. Thus it is possible to treat a compound having an esterified hydroxymethyl radical $R_4$, wherein the esterified hydroxyl group in particular denotes lower alkanoyloxy, for example acetoxy, with pyridine at an elevated temperature, or first to react it with thiobenzoic acid and then to treat it with pyridine in the presence of a mercury salt, or to react it with a suitable salt, such as potassium thiocyanate, potassium iodide or potassium nitrate, and with pyridine in the presence iodide or potassium nitrate, of water at a pH value of about 6.5 which is set up, for example, with the aid of phosphoric acid, and thus to obtain the corresponding pyridiniummethyl compound which can, if required, be converted into the internal salt (zwitter-ion form), for example by treatment with a suitable ion exchange reagent. Furthermore it is possible to react compounds having a lower alkanoyloxymethyl group, for example acetoxymethyl group, as the radical $R_4$, with a mercapto compound such as an optionally substituted lower alkylmercaptan, phenylmercaptan or heterocyclylmercaptan and thus to obtain compounds of the formula I, wherein $R_4$ in a partial formula I$b$ represents an etherified mercapto group.

Salts of compounds of the formula I can be manufactured in a manner which is in itself known. Thus it is possible to form salts of compounds of the formula I, wherein $R_3$ represents a free carboxyl group, for example by treatment with metal compounds, such as alkali metal salts of suitable carboxylic acids, for example the sodium salt of α-ethyl-caproic acid, or with ammonia or a suitable organic amine.

Salts can be converted in the usual manner into the free compounds, metal and ammonium salts being converted, for example, by treatment with suitable acids or ion exchangers.

Resulting mixtures of isomers can be separated into the individual isomers according to methods which are in themselves known, for example by fractional crystallisation, adsorption chromatography (column chromatography or thin layer chromatography) or other suitable methods of separation. Resulting racemates can be separated into the antipodes in the customary manner, if necessary after introduction of suitable salt-forming groupings, for example by forming a mixture of diastereoisomeric salts with optically active salt-forming agents, separating the mixture into the diastereoisomeric salts and converting the separated salts into the free compounds, or by fractional crystallisation from optically active solvents.

The process also encompasses those embodiments according to which compounds which arise as intermediate products are used as starting substances and the remaining process steps are carried out with these, or the process is stopped at any stage; furthermore, starting substances can be used in the form of derivatives or be formed during the reaction.

Preferably, such starting substances are used, and the reaction conditions are so chosen, that the compounds initially listed as being particularly preferred are obtained.

The starting substances of the formula II are known or can be manufactured according to the processes already mentioned.

The acylating agents to be used for introducing the acyl group III or IV are also known or can be manufactured according to methods which are in themselves known. These acylating agents do not have to be in the isolated form but can be used, for example, in the form of solutions or suspensions in which they are obtained in the course of their manufacture.

A derivative suitable for introducing the acyl group III, for example an acid chloride of the formula $Cl-SO_2-NH-CO-R$, wherein R has the abovementioned meaning, can be obtained in a simple manner by reaction of the compound $R-H$ or $R-COOH$ with chlorosulphonylisocyanate in accordance with the equations

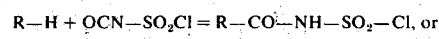

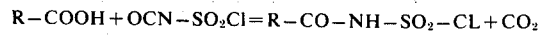

Solvents used are, for example, acetonitrile, ethers, hydrocarbons such as benzene, halogenated, especially chlorinated, hydrocarbons such as carbon tetrachloride, chloroform, methylene chloride and mixtures of these solvents. The reagents themselves can optionally also serve as solvents. The reaction is preferably carried out in the presence of a catalyst, for example a tertiary amine such as triethylamine. It is carried out, for example, at room temperature, but lower or higher temperatures, for example from −20° to +100° C, can also be used.

A derivative suitable for introducing the acyl group IV, for example an activated ester of the formula

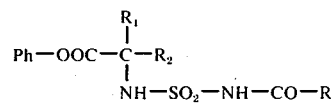

wherein Ph represents a nitro-substituted or halogen-substituted phenyl radical and R, $R_1$ and $R_2$ have the abovementioned meaning, can be manufactured, for example, by reaction of the ester

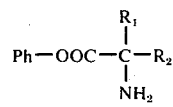

with R-CO-sulphamyl chloride.

The new compounds can be used as medicines, for example in the form of pharmaceutical preparations which contain an effective amount of the active substance together with, or mixed with, inorganic or organic, solid or liquid, pharmaceutically usable excipients which are suitable for enternal or, preferably, parenteral administration. Thus, tablets or gelatine capsules are used which contain the active substance together with diluents, for example lactose, dextrose, sucrose, mannitol, sorbitol, cellulose and/or glycine, and lubricants, for example silica, talc, stearic acid or salts thereof, such as magnesium stearate or calcium stearate, and/or polyethylene glycol; tablets also contain binders, for example magnesium aluminium silicate, starches, such as corn starch, wheat starch, rice starch or arrowroot, gelatine, tragacanth, methylcellulose, sodium carboxymethylcellulose and/or polyvinylpyrrolidone and, if desired, disintegrating agents, for example, starches, agar, alginic acid or a salt thereof, such as sodium alginate, and/or effervescent mixtures, or adsorbents, dyestuffs, flavouring substances and sweeteners. Preferably, the pharmacologically active compounds of the present invention are used in the form of injectable, for example intravenously administrable, preparations, or of infusion solutions. Such solutions are preferably isotonic aqueous solutions or suspensions which can, for example, be manufactured before use from lyophilised preparations which contain the active substance alone or together with an excipient, for example mannitol. The pharmaceutical preparations can be sterilised and/or contain auxiliary substances, for example preservatives, stabilisers, wetting agents and/or emulsifiers, solubilising agents, salts for regulating the osmotic pressure and/or buffers. The present pharmaceutical preparations which can, if desired, contain further pharmacologically valuable substances, are manufactured in a manner which is in itself known, for example by means of conventional mixing, granulating, dragee-making, dissolving or lyophilising processes, and contain from about 0.1% to 100%, especially from about 1% to about 50%, of lyophilisates or up to 100% of the active substance.

In the context of the present description, organic radicals described as "lower" contain up to 6, preferably up to 4, carbon atoms; acyl radicals contain up to 20, preferably up to 12, carbon atoms.

The examples which follow serve to illustrate the invention; temperatures are given in degrees centigrade.

The following systems are used in thin layer chromatography:

| System | | |
|---|---|---|
| | 52 | n-Butanol-glacial acetic acid-water (75:7.5:21) |
| | 96 | sec.Butanol-glacial acetic acid-water (67:10:23) |
| | 100 | Ethyl acetate-pyridine-glacial acetic acid-water (62:21:6:11) |
| | 110 | Ethyl acetate-n-butanol-pyridine-glacial acetic acid-water (42:21:21:6:10) |
| | 200 | n-Butanol-carbon tetrachloride-methanol-formic acid-water (30:40:20:5:5). |

In the Examples, "MIC" means the minimum inhibitory concentration which is measured in γ/ml by the gradient plate test described in "Antibiotics" Vol. I by Gottlieb and Shaw, New York, 1967, page 508, a modified method of that described by V. Bryson and R. Szybalski, Science 116, 45 (1952). The MIC is determined on strains of *Pseudomonas aeruginosa* (abbreviated *Ps.aer.*) ATCC 12055, *Ps.aer.* ATCC 10145, *Ps.aer.* NCTC 10701, *Ps.aer.* 313, *Staphylococcus aureus* Smith 14 (abbreviated *St. aur.* 14), *Escherichia colia* ATCC 2018 (abbreviated *E. coli* 2018), *E. coli* 205 and/or *Klebsiella pneumoniae* (abbreviated *Kl. pn*) 327.

EXAMPLE 1

A solution of nicotinoylsulphamyl chloride in methylene chloride, which is obtained by treating a solution of 2.45 g of nicotinic acid in 50 ml of acetonitrile with 3 drops of triethylamine and a solution of 3.45 ml of chlorosulphonylisocyanate in 5 ml of acetonitrile, warming to 80° C for 1 hour, evaporating to dryness and taking up the residue in 25 ml of methylene chloride, is added dropwise in a nitrogen atmosphere at −70° C whilst stirring, to a solution of (N-trimethyl-silylated) 6-(D-α-phenylglycylamino)-penicillanic acid trimethylsilyl ester manufactured as described below from 6.1 g of 6-(D-α-phenylglycylamino)-penicillanic acid. After the addition is complete, the mixture is stirred for a further 1½ hours at 0° C and is then evaporated at 0.1 mm Hg, and the residue is taken up in 0.5 liter of ether and 0.4 liter of 1 M phosphate buffer of pH 7 at 0° C. The phases are separated and the aqueous phase is extracted twice more with ether. The aqueous phase is adjusted to pH 2.0 with concentrated hydrochloric acid at approx. 0° C and, after saturation with sodium chloride, is extracted with ethyl acetate. The ethyl acetate solution is washed with saturated sodium chloride solution and dried over anhydrous calcium sulphate and on concentration yields crystalline 6-[D-α-nicotinoylsulphamylamino)-phenylacetamido]-penicillanic acid of melting point 163°–165° (decomposition). The optical rotation $[\alpha]_D^{20} = +187° \pm 1°$ ($c = 1$ in 0.5 N NaHCO$_3$). In a thin layer chromatogram on silica gel. Rf$_{52}$ = 0.54; Rf$_{96}$ = 0.59; Rf$_{100}$ = 0.45 and Rf$_{200}$ = 0.69. MTC: *Ps.aer.* 12055 = 9; *Ps.aer.* 10145 = 9; *Ps.aer.* 10701 = 0.4; *Ps.aer.*313 = 9; *St. aur.* 14 = 0.3; *E.coli* 2018 = 2; *E.coli* 205 = 6.5; *Kl.pn.*327 = 50.

The 6-(D-α-phenylglycylamino)-penicillanic acid silyl ester solution can be manufactured as follows: 2.5 ml of triethylamine and 3.8 ml (30 mmols) of trimethylchlorosilane are added to a suspension of 6.1 g (15 mmols) of 6-(D-α-phenylglycylamino)-penicillanic acid trihydrate in 150 ml of methylene chloride, the mixture is stirred for 30 minutes at 28° C and 18 ml of pyridine are then added.

EXAMPLE 2

A solution of pyridyl-(2)-carbonylsulphamyl chloride in tetrahydrofurane, which is obtained by pouring 7.0 ml of chlorosulphonylisocyanate over 5.08 g of pyridine-2-carboxylic acid, adding 6 drops of acetonitrile, allowing the mixture to stand for 2 hours, then removing the acetonitrile and excess isocyanate at 0.1 mm Hg and dissolving the residue in 60 ml of tetrahydrofurane, is added to a solution, manufactured as described below and cooled to −30° C, of 6-(D-phenylglycylamino)-penicillanic acid silyl ester in methylene chloride, and thereafter the mixture is stirred for 1 hour at −10° C. The batch is then worked up as described in Example 1. 5.2 g of 6-[D-α-[pyridyl-(2)-carbonylsulphamylamino]-phenylacetamido]-penicillanic acid is obtained. For purification, this is dissolved in 50 ml of acetone and converted into the crystalline sodium salt by means of 8 ml of 3 M methanolic sodium-α-ethylhexanoate. The crystals are separated off and washed with acetone and ether. For reconversion into the acid, the salt is dissolved in 0.5 M potassium dihydrogen phosphate at 0° C, the solution is covered with ethyl acetate, the pH is adjusted to 2.0 by adding concentrated hydrochloric acid and shaking, and the phase is separated off. After saturation with sodium chloride, the aqueous phase is extracted with ethyl acetate and the organic phases are dried with calcium sulphate and evaporated in vacuo. 2.1 g of acid are obtained and are further purified by digestion with ether. The resulting pure 6-[D-α-[pyridyl-(2)-carbonylsulphamylamino]-phenylacetamido]-penicillanic acid has the following Rf-values in a thin layer chromatogram on silica gel: Rf$_{52}$ = 0.58; Rf$_{96}$ = 0.82; Rf$_{100}$ = 0.78; Rf$_{200}$ = 0.92. $[\alpha]_D^{20} = +139° \pm 1°$ ($c = 1$ in 0.5 N Na HCO$_3$). MIC : *Ps.aer.* 12055 = 20; *Ps.aer.* 10145 = 15; *Ps.aer.* 10701 = 2.5; *Ps.aer.* 313 = 20; *St.aur.* 14 = 0.4; *E.coli* 2018 = 5; *E.coli* 205 = 20; *Kl.pn* 327 = 40.

The 6-(D-α-phenylglycylamino)-penicillanic acid silyl ester solution can be manufactured as follows: 7.0 g of anhydrous 6-(D-phenylglycylamino)-penicillanic acid are taken up in 120 ml of methylene chloride, 5.1 ml of trimethylchlorosilane, 10.7 ml of triethylamine and 0.76 g of p-dimethylaminopyridine are added at −10° C and the mixture is stirred for 30 minutes at −10° C.

EXAMPLE 3

A solution of isonicotinoylsulphamyl chloride in tetrahydrofurane, which is manufactured analogously to the pyridyl-(2)-carbonylsulphamyl chloride solution in Example 2, but by heating the reaction mixture for one hour to 90° C, is run, under nitrogen, into a solution of 6-(D-α-phenylglycylamino)-penicillanic acid silyl ester manufactured as described in Example 2 and cooled to −30° C, and thereafter the procedure described in Example 2 is followed. 2.3 g of crystalline 6-[D-α-[pyridyl-(4)-carbonylsulphamyl-amino]-phenylacetamido]-penicillanic acid of melting point 164°–167° C are obtained. In a thin layer chromatogram on silica gel, $Rf_{52} = 0.54$; $Rf_{96} = 0.60$; $Rf_{100} = 0.48$; $Rf_{200} = 0.69$. $[\alpha]_D^{20} = +158° \pm 1°$ ($c = 1$ in 0.5 N $NaHCO_3$). MIC : Ps.aer. 12055 = 25; Ps.aer. 10145 = 25; Ps.aer. 10701 = 3; Ps.aer. 313 = 30; St. aur. 14 = 0.5; E.coli 2018 = 4; E.coli 205 = 30; Kl.pn. 327 = 50.

EXAMPLE 4

A solution of nicotinoylsulphamyl chloride manufactured in accordance with Example 1 is allowed to react at −70° C, under nitrogen, with the solution of 7-(D-α-phenylglycylamino)-cephalosporanic acid silyl ester described below, which is added dropwise. After completion of the addition, the mixture is stirred for a further 30 minutes at 0° C. Working up, carried out as in Example 1, yields 3.2 g of crystalline 7-(D-α-nicotinylsulphamylamino-phenylacetamido)-cephalosporanic acid of melting point 184°–187° C. In a thin layer chromatogram on silica gel, $Rf_{52} = 0.37$; $Rf_{96} = 0.45$; $Rf_{100} = 0.31$; $Rf_{110} = 0.45$. $[\alpha]_D^{20} = \pm 68° \pm 1°$ ($c = 1$ in 0.5 N $NaHCO_3$).

The silyl ester solution is manufactured as follows: A suspension of 8.8 g of 7-(D-phenylglycylamino)-cephalosporanic acid dihydrate in 200 ml of methylene chloride is treated with 7 ml of triethylamine and 10 ml of trimethylchlorosilane, stirred for 30 minutes at 21° C and treated with 31 ml of pyridine.

EXAMPLE 5

A solution of 2-methoxycarbonyl-pyridyl-(3)-carbonylsulphamyl chloride in acetonitrile, which is obtained if 3.5 g of 2-methoxycarbonylpyridine-3-carboxylic acid in 100 ml of acetonitrile are treated with 4 drops of triethylamine and 3.4 ml of chlorosulphonylisocyanate, the mixture is stirred for 1 hour at 35° C and evaporated at 0.1 mm Hg and the residue is dissolved in 50 ml of acetonitrile, is added dropwise in a nitrogen atmosphere whilst stirring at −70° C to a solution of 6-(D-α-phenylglycylamino)-penicillanic acid trimethylsilyl ester manufactured as described below, and the mixture is subsequently stirred for a further 30 minutes at 0° C. Working up as described in Example 1 yields 4.5 g of crystalline 6-((D-α-[2-methoxycarbonyl-pyridyl-(3)-carbonylsulphamylamino]-phenylacetamido))-penicillanic acid of melting point 150°–152° C.

In a thin layer chromatogram on silica gel, $Rf_{52} = 0.46$; $Rf_{96} = 0.55$; $Rf_{100} = 0.38$; $Rf_{110} = 0.52$. $[\alpha]_D^{20} = \pm 146 \pm 1°$ ($c = 1$ in 0.5 N $NaHCO_3$).

The silyl ester solution is manufactured as follows: A suspension of 6.1 g (15 mmols) of 6-(D-α-phenylglycylamino)-penicillanic acid trihydrate in 150 ml of methylene chloride is treated with 2.5 ml of triethylamine and 3.8 ml of trimethylchlorosilane and stirred for 35 minutes at 25°–28° C. Before being used further, 18 ml of pyridine are added.

EXAMPLE 6

A solution of 6-hydroxypyridyl-(3)-carbonylsulphamyl chloride which is obtained if a suspension of 2.71 g of 6-hydroxypyridine-3-carboxylic acid in 70 ml of acetonitrile is treated with 4 drops of triethylamine and 1.71 ml of chlorosulphamylisocyanate and stirred for 1 hour at 40° C, is allowed to react, in the same manner as described in Example 5, with the trimethylsilyl ester solution from 6.1 g of 6-(D-α-phenylglycyl-amino)-penicillanic acid trihydrate which has been described in Example 1. 6-((D-α-]6-Hydroxypyridyl-(3)-carbonylsulphamylamino]-phenylacetamido))-penicillanic acid of melting point 167°–171° C is obtained.

In a thin layer chromatogram on silica gel, $Rf_{52} = 0.63$; $Rf_{96} = 0.67$; $Rf_{100} = 0.19$; $Rf_{110} = 0.25$.

EXAMPLE 7

In the same manner as described in Example 5, a solution of formyl-sulphamyl chloride which is obtained if a solution of 1.6 ml of chlorosulphonylisocyanate in 10 ml of acetonitrile is added dropwise at −20° C to a solution of 0.8 ml of formic acid in 10 ml of acetonitrile and the mixture is allowed to warm to 0° C over the course of one hour, is reacted with the trimethylsilyl ester solution from 6.1 g of 6-(D-α-phenylglycylamino)-penicillanic acid trihydrate, described in Example 1. 2.2 g of crystalline 6-[D-α-(formylsulphamylamino)-phenylacetamido]-penicillanic acid of melting point 136°–139° C are obtained.

In a thin layer chromatogram on silica gel, $Rf_{52} = 0.25$; $Rf_{96} = 0.43$; $Rf_{100} = 0.12$; $Rf_{110} = 0.22$.

EXAMPLE 8

A solution of acetyl-sulphamyl chloride which is obtained if 3.5 ml of chlorosulphonylisocyanate are added dropwise, whilst cooling with ice, to 2.3 ml of glacial acetic acid, after 30 minutes standing at 20° C the crystals are freed of volatile constituents in vacuo and the residue is dissolved in 130 ml of methylene chloride, is added at −30° C, under nitrogen, to a solution of 6-(D-α-phenylglycyl-amino)-penicillanic acid trimethylsilyl ester manufactured as described below. After working up as in Example 1, 7.4 g of 6-(D-α-acetylsulphamylamino-phenylacetamido)-penicillanic acid of melting point 140°–142° C. are obtained.

In a thin layer chromatogram on silica gel, $Rf_{52} = 0.69$; $Rf_{96} = 0.69$; $Rf_{100} = 0.44$; $Rf_{200} = 0.80$. $[\alpha]_D^{20} = \pm 171° \pm 1°$ ($c = 1$ in 0.5 N $NaHCO_3$).

The silyl ester solution is manufactured by reacting a suspension of 11.2 g (32 mmols) of anhydrous 6-(D-α-phenylglycylamino)-penicillanic acid in 180 ml of methylene chloride, in the presence of 16.8 ml (0.12 mol) of triethylamine and 1.2 g of p-dimethylamino-pyridine, with 8.0 ml (64 mmols) of trimethylchlorosilane at −10° C for 30 minutes.

EXAMPLE 9

A solution of methoxyacetyl-sulphamyl chloride which is obtained if 2.25 g of methoxyacetic acid are treated with 2.2 ml of chlorosulphonyl chloride, the mixture is warmed to 70° C for 15 minutes and left to stand for 1½ hours at 22° C and is dissolved in 50 ml of methylene chloride, is reacted, ad described in Example 8, with a silyl ester slution of 20 mmols of 6-(D-α-phenylglycylamino)-penicillanic acid, manufactured in accordance with Example 8. 6-(D-α-Methoxyacetylsulphamylamino-Phenyl-acetamido)-penicillanic acid is obtained, which can be converted into the crystalline sodium salt by dissolving in 50 ml of acetone and adding excess sodium α-ethyl-hexanoate.

In a thin layer chromatogram on silica gel, $Rf_{52} = 0.62$; $Rf_{96} = 0.67$; $Rf_{100} = 0.59$; $Rf_{200} = 0.81$. $[\alpha]_D^{20} = \pm 139° \pm 1°$ ($c = 1$ in 0.5 N $NaHCO_3$).

EXAMPLE 10

A solution of cyanoacetylsulphamyl chloride which is obtained if 2.12 g of cyanoacetic acid are dissolved in 25 ml of acetonitrile, 4.55 ml of chlorosulphonylisocyanate are added, the mixture is stirred for one hour at 90° C and evaporated, and the residue is taken up in 40 ml of tetrahydrofurane, is reacted analogously to Example 8 with a silyl ester solution from 20 mmols of 6-(D-α-phenylglycylamino)-penicillanic acid, manufactured according to Example 8, and worked up. The crystalline crude product, in methanol solution, is treated with active charcoal. The evaporated filtrate is digested with ethyl acetate + ether (1:2) and 6-(D-α-cyanoacetylsulphamylamino-phenylacetamido)-penicillanic acid is obtained as the soluble component.

In a thin layer chromatogram on silica gel, $Rf_{52} = 0.66$; $Rf_{96} = 0.73$; $Rf_{100} = 0.54$; $Rf_{200} = 0.76$. $[\alpha]_D^{20} = \pm 125° \pm 1°$ ($c = 1$ in 0.5 N $NaHCO_3$).

EXAMPLE 11

A solution of pentane-2,4-dion-3-yl-sulphamyl chloride, which is obtained if 2.5 g of acetylacetone are treated with 2.2 ml of chlorosulphonylisocyanate, the mixture is cooled with ice water and the resulting crystals are dissolved in 50 ml of methylene chloride, is reacted analogously to Example 8 with a silyl ester solution from 20 mmols of 6-(D-α-phenylglycylamino)-penicillamic acid manufactured according to example 8, and worked up. 6-[D-α-(pentane-2,4-dion-3-yl-carbonylsulphamylamino)-phenylacetamido]-penicillanic acid, which is very sparingly soluble in ethyl acetate and has a melting point of 153°–159° C, is obtained.

In a thin layer chromatogram on silica gel, $Rf_{52} = 0.16$; $Rf_{96} = 0.33$; $Rf_{100} = 0.05$; $Rf_{200} = 0.16$. $[\alpha]_D^{20} = \pm 137° \pm 1°$ ($c = 1$ in 0.5 N $NaHCO_3$).

EXAMPLE 12

A solution of dicyanoacetylsulphamyl chloride which is obtained if 1.7 g of sodium malonitrile are taken up in 30 ml of methylene chloride, treated with 3.8 ml of trimethylchlorosilane, stirred for 15 minutes at 25° C and 25 minutes at 40° C and cooled to −5° C, 1.8 ml of chlorosulphamylisocyanate and 2.8 ml of triethylamine are added and the mixture is stirred for 1 hour at 0° C, is reacted analogously to Example 5 with a silyl ester solution from 15 mmols of 6-(D-α-phenylglycylamino)-penicillanic acid, manufactured according to Example 5, and worked up. 3.8 g of 6-(D-α-dicyanoacetylsulphamylamino-phenylacetamido)-penicillanic acid are obtained.

In a thin layer chromatogram on silica gel, $Rf_{52} = 0.67$; $Rf_{96} = 0.68$; $Rf_{100} = 0.20$; $Rf_{110} = 0.23$.

EXAMPLE 13

A solution of benzoylsulphamyl chloride which is obtained if 3.5 ml of chlorosulphonyl chloride are poured over 4.8 g of benzoic acid, the mixture is warmed for 30 minutes to 40° C and the crystals are dissolved in 180 ml of methylene chloride, is stirred for 1 hour at −10° C with a silyl ester solution manufactured from 32 mmols of 6-(D-α-phenylglycylamino)-penicillanic acid according to Example 8, and the product is worked up as in Example 1. 11.0 g of crude acid are obtained and are dissolved in 75 ml of acetone and treated with 51 mmols of the sodium salt of α-ethylcaproic acid. 9.2 g of the sodium salt of 6-(D-α-benzoylsulphamylamino-phenylacetamido)-penicillanic acid crystallise out.

In a thin layer chromatogram on silica gel, $Rf_{52} = 0.65$; $Rf_{96} = 0.68$; $Rf_{100} = 0.49$; $Rf_{200} = 0.86$. $[\alpha]_D^{20} = + 129° \pm 1°$ ($c = 1$ in 0.5 N $NaHCO_3$).

EXAMPLE 14

A solution of p-dimethylaminobenzoyl-sulphamyl chloride which is obtained if a suspension of 4.23 g of p-dimethylaminobenzoic acid in 7.5 ml of benzene is treated with 2 ml of acetonitrile and 4.4 ml of chlorosulphonyl-isocyanate, the mixture is boiled for 1½ hours under reflux and evaporated and the crystalline residue is taken up in 50 ml of tetrahydrofurane, is reacted, as described in Example 8, with a silyl ester solution from 20 mmols of 6-(D-α-phenylglycylamino)-penicillanic acid, manufactured according to Example 8. The reaction product is evaporated at 0.1 mm Hg, the residue is taken up in 100 ml of methanol and the solution is adjusted to pH 4.3 with pyridine and again evaporated. The residue is successively digested with ether, ethyl acetate, ethyl acetate-acetone (3:1) and acetone. The constituents soluble in the last three solvents contain 12.9 g of crude acid. The acid is decolourised with charcoal in ethyl acetate-acetone (1:3) solution and is precipitated from acetone as the sodium salt by means of sodium ethylhexanoate. 4 g of the sodium salt of 6-[D-α-(p-dimethylaminobenzoylsulphamylamino)-phenylacetamido]-penicillanic acid are obtained.

In a thin layer chromatogram on silica gel, $RF_{52} = 0.59$; $Rf_{96} = 0.69$; $Rf_{100} = 0.65$; $Rf_{200} = 0.91$. $[\alpha]_D^{20} = + 88° \pm 1°$ ($c = 1$ in 0.5 N $NaHCO_3$).

EXAMPLE 15

A suspension of o-carbamoylbenzoylsulphamyl chloride which is obtained if 3.22 g of phthalamic acid are suspended in 100 ml of acetonitrile, treated with 4 drops of triethylamine and 3.4 ml of chlorosulphonylisocyanate, stirred for 1 hour at 35° C and evaporated and the crystals are suspended in 50 ml of acetonitrile, is reacted analogously to Example 5 with a silyl ester solution from 15 mmols of 6-(D-α-phenylglycylamino)-penicillanic acid manufactured according to Example 5, and worked up. 1.4 g of 6-[D-α-(o-carbamoylbenzoylsulphamyl-amino)-phenylacetamido]-penicillanic acid are obtained.

In a thin layer chromatogram on silica gel, $Rf_{52} = 0.70$; $Rf_{96} = 0.67$; $Rf_{100} = 0.15$; $Rf_{110} = 0.18$.

EXAMPLE 16

A solution of furane-2-carbonylsulphamyl chloride which is obtained if a solution of 2.83 g of furane in 5 ml of ether is added dropwise at 35° C to a solution of 3.6 ml of chlorosulphonylisocyanate in 25 ml of ether and the mixture is stirred for 1 hour at 30°–35° C, is reacted analogously to Example 8 with a silyl ester solution from 20 mmols of 6-(D-α-phenylglycylamino)-penicllanic acid, manufactured according to Example 8, and worked up. 3.1 g of crystalline 6-[D-α-(furane-2-carbonylsulphamylamino)-phenylacetamido]-penicillanic acid of melting point 156°–159° C are obtained.

In a thin layer chromatogram on silica gel, $Rf_{52} = 0.61$; $Rf_{96} = 0.66$; $Rf_{100} = 0.26$; $Rf_{200} = 0.85$. $[\alpha]_D^{20} = +168° \pm 1°$ ($c = 1$ in 0.5 N $NaHCO_3$).

EXAMPLE 17

A solution of pyrrole-3-carbonylsulphamyl chloride which is obtained if a solution of 1.68 g of pyrrole in 40 ml of methylene chloride is treated with a solution of 2.2 ml of chlorosulphonylisocyanate in 25 ml of methylene chloride and stirred for 45 minutes at 20° – 25° C, is added analogously of Example 8 to a silyl ester solution (approx. 20 mmols) manufactured as in Example 8, and the batch is worked up as there. After digestion with ether, 4.2 g of 6-[D-α-(pyrrole-3-carbonylsulphamylamino)-phenylacetamido]-penicillanic acid are obtained.

In a thin layer chromatogram on silica gel, $Rf_{52} = 0.64$; $Rf_{96} = 0.73$; $Rf_{100} = 0.60$; $Rf_{200} = 0.81$. $[\alpha]_D^{20} = +128° \pm 1°$ ($c = 1$ in 0.5 N $NaHCO_3$).

EXAMPLE 18

A suspension of imidazolecarbonylsulphamyl chloride, which is obtained if 1.7 g of imidazole in 2.0 ml of acetonitrile are treated with 4.4 ml of chlorosulphonylisocyanate, diluted with 20 ml of acetonitrile, then stirred for 1 hour at 90° C and evaporated and the crystalline residue is taken up in 50 ml of tetrahydrofurane, is allowed to react analogously to Example 8 with a silyl ester solution from 20 mmols of 6-(D-α-phenylglycylamino)-penicillanic acid, and worked up. 4.6 g of 6-(D-α-imidazolecarbonylsulphamylamino)-penicillanic acid of melting point 173°–175° C are obtained.

In a thin layer chromatogram on silica gel, $Rf_{52} = 0.2$; $Rf_{96} = 0.65$; $Rf_{100} = 0.21$; $Rf_{200} = 0.92$. $[\alpha]_D^{20} = +172° \pm 1°$ ($c = 1$ in 0.5 N $NaHCO_3$).

EXAMPLE 19

A solution of 0.8 g of methoxycarbonylsulphamyl chloride in 10 ml of methylene chloride is added at −10° C to a silyl ester solution which is obtained if a suspension of 4 mmols of 6-(D-α-phenylglycylamino)-cephalosporanic acid in 30 ml of methylene chloride is treated with 3.2 ml of pyridine and 1 ml of trimethylchlorosilane and stirred for 30 minutes at 22° C until a clear solution is obtained, and the mixture is left to react for 30 minutes at 0° C and 30 minutes at 20° C. Working up, effected as in Example 1, yields 1.4 g of 6-(α-methoxycarbonylsulphamylamino-phenylacetamido)-penicillanic acid. This product, in acetone solution, is converted into the crystalline sodium salt by means of sodium α-ethylhexanoate.

In a third layer chromatogram on silica gel, $Rf_{52} = 0.58$; $Rf_{96} = 0.67$; $Rf_{110} = 0.59$; $Rf_{200} = 0.72$. $[\alpha]_D^{20} = +171° \pm 1°$ ($c = 1$ in 0.5 N $NaHCO_3$).

EXAMPLE 20

A solution of 2,2,2-trichloroethoxycarbonylsulphamylchloride, which is obtained if 2.0 ml of 2,2,2-trichloroethanol are added dropwise to a solution of 1.7 ml of chlorosulphonyl chloride in 5 ml of carbon tetrachloridemethylene chloride (4:1, volume:volume) and the mixture is vibrated for 15 minutes at 50° C and then diluted with 10 ml of ether, is reacted analogously to Example 5 with a silyl ester solution from 15 mmols of 6-(D-α-phenylglycylamino)penicillanic acid and worked up. After repeated crystallisation from ether + hexane, 3.2 g of 6-[D-α-(2,2,2-trichloroethoxycarbonylsulphamylamino)-phenylacetamido]-penicillanic acid of melting point 146° C are obtained.

In a thin layer chromatogram on silica gel, $Rf_{52} = 0.68$; $Rf_{96} = 0.75$; $Rf_{100} = 0.59$; $Rf_{200} = 0.96$. $[\alpha]_D^{20} = +138° \pm 1°$ ($c = 1$ in 0.5 N $NaHCO_3$).

EXAMPLE 21

A solution of 0.8 g of methoxycarbonylsulphamyl chloride is reacted analogously to Example 19 with a silyl ester solution which is obtained at 20° C, with 15 minutes reaction time, from 4 mmols of 7-(D-phenylglycylamino)cephalosporanic acid, 1 ml of trimethylchlorosilane, 3.2 ml of pyridine and 30 ml of methylene chloride, and worked up. The resulting 7-[D-α-(methoxy-carbonylsulphamylamino)-phenylacetamido]-cephalosporanic acid, in methanol solution, is treated with 2 mmols of sodium α-ethylhexanoate, the mixture is evaporated and the residue is digested with hexane-ether. The sodium salt of the acid is obtained.

In a thin layer chromatogram on silica gel, $Rf_{52} = 0.45$; $Rf_{96} = 0.60$; $Rf_{110} = 0.57$; $Rf_{200} = 0.60$. $[\alpha]_D^{20} = +89° \pm 1°$ ($c = 1$ in 0.5 N $NaHCO_3$).

EXAMPLE 22

A solution of 2,2,2-trichloroethoxycarbonylsulphamyl chloride which is obtained if 1.7 g of chlorosulphonylisocyanate and 1.8 g of 2,2,2-trichloroethanol are dissolved in 20 ml of methylene chloride and stirred for 30 minutes at 35°–37° C, is added dropwise at −15° C to a silyl ester solution which is obtained if 4 g of anhydrous 7-(D-α-phenylglycylamino)-cephalosporanic acid are taken up in 100 ml of methylene chloride, 8 ml of pyridine and 2.5 ml of trimethylchlorosilane are added and the mixture is stirred for 30 minutes at 20° C. Thereafter, the new mixture is stirred for 30 minutes at 2° C. Working up as in Example 1 yields 5.5 g of 7-[D-α-(2,2,2-trichloroethoxycarbonylsulphamylamino)-phenylacetamido]-cephalosporanic acid, which is converted into the crystalline sodium salt by means of sodium α-ethylhexanoate in acetone-ether.

In a thin layer chromatogram on silica gel, $Rf_{52} = 0.58$; $Rf_{96} = 0.61$; $Rf_{110} = 0.51$; $Rf_{200} = 0.67$. $[\alpha]_D^{20} = +60 \pm 1°$ (= 1 in 0.5 N $NaHCo_3$).

EXAMPLE 23

A solution of 2-dimethylamino-ethoxycarbonylsulphamyl chloride, which is obtained if a solution of 1.7 ml of chlorosulphonylisocyanate in 5 ml of acetonitrile is mixed with a solution of 2.0 ml of 2-dimethylaminoethanol in 5 ml of acetonitrile and the mixture is vibrated for 30 minutes at 2° C, is reacted, analogously to Example 5, with a silyl ester solution from 15 mmols of 6-(D-α-phenyl-glycylamino)-penicillanic acid, manufactured as in Example 5. The evaporated reaction mixture is dissolved in 150 ml of methanol and again evaporated. The residue is repeatedly triturated with ether and then with ethyl acetate and with ethyl acetate + acetone (1+2) and is finally suspended in 50 ml of water. The mixture is filtered, the filter residue is dissolved in methanol, the solution is decolourised with charcoal, and after evaporating the solvent 1.9 g of 6-[D-α-(2-dimethylaminoethoxycarbonyl-sulphamylamino)-phenyl-acetamido]-penicillanic acid are obtained.

In a thin layer chromatogram on silica gel, $Rf_{52} = 0.14$; $Rf_{96} = 0.25$; $Rf_{100} = 0.03$; $Rf_{200} = 0.21$. $[\alpha]_D^{20} = +127° \pm 1°$ ($c = 1$ in 0.5 N $NaHCO_3$).

EXAMPLE 24

A silyl ester solution which is obtained if a suspension of 6.1 g of 6-(D-phenylglycylamino)-penicillanic acid trihydrate in 150 ml of methylene chloride is treated with 2.5 ml of triethylamine and stirred for 45 minutes at 25° C, 12 ml of pyridine and 3.8 ml of trimethylchlorosilane are added and the mixture is stirred for a further 30 minutes at 25° C, is treated with 3.7 g of isopropoxycarbonylsulphamyl chloride at −10° C, and stirred for 2 hours at 0° C. Working up as in Example 1 yields, after trituration with ether, 6.5 g of 6-[D-α-(isopropoxycarbonylsulphamylamino)-phenylacetamido]-penicillanic acid.

In a thin layer chromatogram on silica gel, $Rf_{52} = 0.83$; $Rf_{96} = 0.83$; $Rf_{100} = 0.60$; $Rf_{200} = 0.89$. $[\alpha]_D^{20} = + 155° \pm 1°$ ($c = 1$ in 0.5 N NaHCO$_3$).

The isopropoxycarbonylsulphamyl chloride can be manufactured as follows: 15 ml of isopropanol are added dropwise to a solution of 1.7 ml of chlorosulphonylisocyanate in 50 ml of carbon tetrachloride-methylene chloride (4:1, volume:volume) and the mixture is cooled from +50° C to −5° C over the course of 45 minutes whilst stirring. Filtration of the crystals yields 33.2 g of isopropoxycarbonylsulphamyl chloride of melting point 66° C.

EXAMPLE 25

A solution of phenoxycarbonylsulphamyl chloride which is obtained if 1.7 g of phenol and 2.6 g of chlorosulphonylisocyanate in 25 ml of methylene chloride are stirred for 45 minutes at 35°–40° C, is added at −30° C to a silyl ester solution from 6.1 g (15 mmols) of 6-(D-α-phenylglycylamino)penicillanic acid trihydrate, manufactured according to Example 5, and the mixture is stirred for 30 minutes at −20° C and 1 hour at 0° C. Working up as in Example 1 and conversion into the sodium salt yields 1.8 g of the sodium salt of 6-(D-α-phenoxycarbonylsulphamylamino-phenylacetamido)-penicillanic acid.

In a thin chromatogram on silica gel, $Rf_{52} = 0.72$; $Rf_{96} = 0.75$; $Rf_{110} = 0.67$; $Rf_{200} = 0.91$. $[\alpha]_D^{20} = + 131° \pm 1°$ ($c = 1$ in 0.5 N NaHCO$_3$).

EXAMPLE 26

Analogously to Example 25, 2,4-dichlorophenoxycarbonylsulphamyl manufactured starting from 2.94 g of 2,4-dichlorophenol, and 15 mmols of silyl ester as in Example 25 yield the sodium salt of 6-[D-α-(2,4-dichlorophenoxycarbonylsulphamylamino)-phenylacetamido -penicillanic acid.

In a thin layer chromatogram on silica gel, $Rf_{52} = 0.66$; $Rf_{96} = 0.71$; $Rf_{110} = 0.30$; $Rf_{200} = 0.85$. $[\alpha]_D^{20} = + 151° \pm 1°$ ($c = 1$ in 0.5 N NaHCO$_3$).

EXAMPLE 27

A suspension of pyrimidine-2-carbamylsulphamyl chloride which is obtained if a suspension of 2.38 g of 2-aminopyrimidine in 10 ml of acetonitrile is added to a solution of 2.3 ml of chlorosulphonylisocyanate in 15 ml of acetonitrile, the mixture is subsequently stirred for 75 minutes at 22° C and evaporated and the residue is suspended in 100 ml of tetrahydrofurane-methylene chloride (1:1), is reacted analogously to Example 5 with a silyl ester solution as in Example 5 (approx. 20 mmols of silyl ester), and worked up. After digestion with acetone, 0.5 g of acetone-insoluble 6-[D-α-(pyrimidine-2-carbamylsulphamylamino)-phenylacetamido]-penicillanic acid of melting point 134°–138° C are obtained.

In a thin layer chromatogram on silica gel, $Rf_{52} = 0.56$; $Rf_{96} = 0.62$; $Rf_{100} = 0.57$; $Rf_{200} = 0.76$. $[\alpha]_D^{20} = + 102° \pm 1°$ ($c = 1$ in 0.5 N NaHCO$_3$).

EXAMPLE 28

A solution of pyrazine-2-carbamylsulphamyl chloride which is obtained if a solution of 1.8 g of 2-aminopyrazine in 40 ml of acetonitrile is added to a solution of 1.7 ml of chlorosulphonylisocyanate in 25 ml of acetonitrile and the mixture is stirred for 45 minutes at 25° C, is reacted analogously to Example 5 with a silyl ester solution as in Example 5, (approx. 15 mmols of silyl ester), and worked up. 1.6 g of 6-[D-α-(pyrazine-(2)-carbamylsulphamylamino)-phenylacetamido]-penicillanic acid of melting point 171°–172° C are obtained.

In a thin layer chromatogram on silica gel, $Rf_{52} = 0.55$; $Rf_{96} = 0.78$; $Rf_{100} = 0.28$; $Rf_{110} = 0.38$. $[\alpha]_D^{20} = + 147° \pm 1°$ ($c = 1$ in 0.5 N NaHCO$_3$).

EXAMPLE 29

A solution of pyridine-2-carbamylsulphamyl chloride which is obtained if a solution of 1.8 g of 2-aminopyridine in 50 ml of acetonitrile is added to a solution of 1.7 ml of chlorosulphonylisocyanate in 50 ml of acetonitrile and the mixture is stirred for 40 minutes at 0° C, is reacted analogously to Example 5 with a silyl ester solution as in Example 5 (approx. 15 mmols of silyl ester), and worked up. 2.0 g of 6-[D-α-(pyridine-2-carbamylsulphamylamino)-phenylacetamido]-penicillanic acid are obtained.

In a thin layer chromatogram on silica gel, $Rf_{52} = 0.58$; $Rf_{96} = 0.79$; $Rf_{100} = 0.14$; $Rf_{110} = 0.23$. $[\alpha]_D^{20} = + 177° \pm 1°$ ($c = 1$ in 0.5 N NaHCO$_3$).

EXAMPLE 30

A solution of rhodanine-3-carbamoylsulphonyl chloride which is obtained if a solution of 3.11 g of 3-aminorhodanine in 50 ml of acetonitrile is added to a solution of 1.8 ml of chlorosulphonylisocyanate in 50 ml acetonitrile and the mixture is stirred for 40 minutes at 25° C, is reacted, analogously to Example 5, with a silyl ester solution as in Example 5 (approx. 1.5 mmols of silyl ester), and worked up. The resulting crude product, in acetone solution, is decolourised with active charcoal and then converted by means of sodium α-ethylhexanoate into the sodium salt of 6-[D-α-(rhodanine-3-carbamylsulphamylamino)-phenylacetamido]-penicillanic acid.

In a thin layer chromatogram on silica gel, $Rf_{52} = 0.56$; $Rf_{96} = 0.76$; $Rf_{100} = 0.20$; $Rf_{110} = 0.28$. $[\alpha]_D^{20} = + 110° \pm 1°$ ($c = 1$ in 0.5 N NaHCO$_3$).

EXAMPLE 31

A suspension of p-acetamidobenzoylsulphamyl chloride in acetonitrile which is obtained if 4.66 g of p-acetamidobenzoic acid in 120 ml of acetonitrile are treated with 5 drops of triethylamine and 2.27 ml of chlorosulphonylisocyanate, stirred for one hour at 40° C and evaporated to dryness, and the residue is taken up in 60 ml of acetonitrile, is reacted analogously to Example 1 with silyl ester solution as in Example 5 (approx. 20 mmols of silyl ester), and worked up. 3.1 g of 6-[D-α-(p-acetamidobenzoylsulphamylamino)-phenylacetamido]-penicillanic acid of melting point 165°–168° C are obtained.

In a thin layer chromatogram on silica gel, $Rf_{52} = 0.70$; $Rf_{96} = 0.64$; $Rf_{100} = 0.53$; $Rf_{110} = 0.56$. $[\alpha]_D^{20} = +137° \pm 1°$ ($c = 1$ in 0.5 N $NaHCO_3$).

EXAMPLES 32 – 45

A silyl ester solution which is manufactured by stirring a mixture of 8.1 g (20 mmols) of 6-(D-α-phenylglycylamino)-penicillanic acid, 3.3 ml (24 mmols) of triethylamine and 5.1 ml (40 mmols) of trimethylchlorosilane in 150 ml of methylene chloride for half an hour at 28° C, is treated at 0° C with 24 ml of pyridine and 20–40 mmols of a sulphonyl chloride of the formula $R-CO-NHSO_2Cl$, wherein R has the meaning indicated in the table which follows, dissolved in 50 ml of acetonitrile, and the mixture is stirred for 30 minutes at 0° C. Working up effected according to Example 1 yields a product of the formula

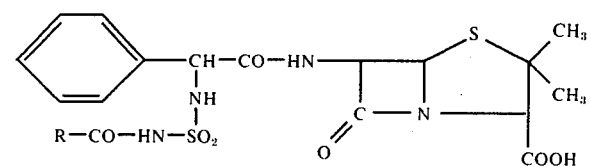

wherein R has the indicated meaning. It is crystallised or precipitated from ethyl acetate or an ethyl acetate-ether mixture, respectively. In the case of the products which crystallise well, the melting points are quoted.

Table

| Example No. | R— | Melting point | $[\alpha]_D^{20}$ | Thin layer chromatograms $Rf_{52}$ | $Rf_{96}$ | $Rf_{100}$ | $Rf_{110}$ |
|---|---|---|---|---|---|---|---|
| 32 | $CH_3(CH_2)_4$— | 145–7° C | +177° | 0.69 | 0.73 | 0.73 | 0.70 |
| 33 | ⌬—$OCH_2$— | — | +177° | 0.58 | 0.64 | 0.17 | 0.19 |
| 34 | Cl—⌬—$OCH_2$— | — | +145° | 0.67 | 0.67 | 0.73 | 0.74 |
| 35 | $CH_3SO_2NH$—⌬— | — | +118° | 0.64 | 0.67 | 0.49 | 0.60 |
| 36 | $O_2N$—⌬— | 152–5° C | +162° | 0.69 | 0.75 | 0.68 | 0.73 |
| 37 | $CH_3O$—⌬— (meta) | 142–6° C | +151° | 0.75 | 0.86 | 0.62 | 0.66 |
| 38 | HOOC—⌬— | — | +151° | 0.72 | 0.73 | 0.65 | 0.67 |
| 39 | HOOC—⌬—HOOC | 194–7° C | +160° | 0.56 | 0.65 | 0.22 | 0.35 |
| 40 | ⌬—NH— | — | +159° | 0.69 | 0.75 | 0.57 | 0.63 |
| 41 | morpholino-N— | 159–62° C | +154° | 0.55 | 0.64 | 0.32 | 0.44 |
| 42 | succinimido-N— | 183–9° C | +157° | 0.47 | 0.58 | 0.19 | 0.25 |
| 43 | ⌬—N($COCH_3$)— | 169–74° C | +166° | 0.45 | 0.50 | 0.34 | 0.46 |
| 44 | $CH_3SO_2NH$— | — | +134° | 0.51 | 0.63 | 0.39 | 0.49 |

Table-continued

| Example No. | R— | Melting point | $[\alpha]_D^{20}$ | Thin layer chromatograms | | | |
|---|---|---|---|---|---|---|---|
| | | | | $Rf_{52}$ | $Rf_{96}$ | $Rf_{100}$ | $Rf_{110}$ |
| 45 | ⟨phenyl⟩—SO₂NH— | — | +127° | 0.66 | 0.68 | 0.54 | 0.60 |

The sulphonyl chloride RCONHSO₂Cl used in Examples 32 – 39 is manufactured by heating a mixture of 24–40 mmols of carboxylic acid of the formula R—COOH, wherein R has the indicated meaning, in 120 ml of acetonitrile, with an equivalent amount of chlorosulphonylisocyanate for 30 minutes at 80° C, then evaporating the mixture and dissolving the residue in 50 ml of acetonitrile.

The sulphonyl chloride RCONHSO₂Cl used in Examples 40 and 41 is manufactured by stirring 26 mmols of amine of the formula R—H and 26 mmols of chlorosulphonyl chloride in 120 ml of acetonitrile for 30 minutes at −40° C, evaporating the mixture and taking up the residue in 50 ml of acetonitrile.

The sulphonyl chloride R—CONHSO₂Cl used in Examples 42 – 45 is manufactured by heating 24 mmols of amide of the formula R—H and 24 mmols of chlorosulphonylisocyanate in acetonitrile to 80° C for 30 minutes, evaporating the mixture and taking up the residue in 50 ml of acetonitrile.

EXAMPLES 46 – 51

A silyl ester solution which is manufactured by stirring a mixture of 8.1 g (20 mmols) of 6-(D-α-phenylglycylamino)-penicillanic acid, 3.3 ml (24 mmols) of triethylamine and 5.1 ml (40 mmols) of trimethylchlorosilane in 150 ml of methylene chloride for half an hour at 28° C, is treated, at 0° C, with 24 ml of pyridine and 40 mmols of a sulphonyl chloride of the formula R—CONHSO₂Cl, wherein R has the meaning indicated in the table which follows, dissolved in 50 ml of acetonitrile, and the mixture is stirred for 30 minutes at 0° C. Working up effected according to Example 1 yields a product of the formula

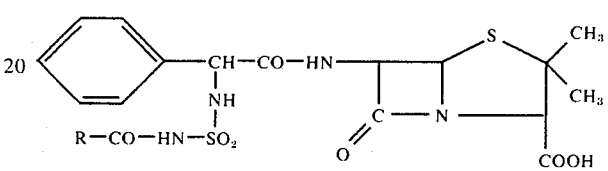

wherein R has the indicating meaning. The product is crystallised or precipitated from ethyl acetate or an ethyl acetate-ether mixture, respectively. In the case of the products which crystallise well, the melting points are quoted.

MIC of 6-[D-α-(o-toluenesulfonylcarbamoylsulfamylamino)-phenylacetamido]-penicillanic acid: Ps.aer.12055 = 30; Ps.aer. 10145 = 10; Ps.aer.313 = 20; St.aur.14 = 0.4; E.coli 2018 = 4; E.coli 205 = 1; Kl.pn.327 = 60.

MIC of 6-[D-α-(β-naphthalenesulfonylcarbamoylsulfamylamino)-phenylacetamido]-penicillanic acid: Ps.aer.12055 = 10; Ps.aer.10145 = 10; Ps.aer.313 = 20; St.aur. 14 = 0.3; E.coli 2018 = 4.5; E.coli 205 = 5; Kl.pn.327 = 30.

| Example No. | R— | Melting point | $[\alpha]_D^*$ | Thin layer chromatogram | | | |
|---|---|---|---|---|---|---|---|
| | | | | $Rf_{52}$ | $Rf_{96}$ | $Rf_{100}$ | $Rf_{110}$ |
| 46 | o-tolyl-SO₂NH— | — | +121° | 0.74 | 0.77 | 0.49 | 0.63 |
| 47 | p-CH₃-C₆H₄—SO₂NH— | — | +124° | 0.84 | 0.73 | 0.64 | 0.68 |
| 48 | β-naphthyl-SO₂NH— | — | +126° | 0.76 | 0.73 | 0.52 | 0.68 |
| 49 | naphthyl-CH₃ | — | +138° | 0.68 | 0.85 | 0.70 | 0.75 |
| 50 | naphthyl-CH₃ | — | +147° | 0.72 | 0.89 | 0.69 | 0.72 |

| Example No. | R— | Melting point | $[\alpha]_D^*$ | Thin layer chromatogram $Rf_{52}$ | $Rf_{96}$ | $Rf_{100}$ | $Rf_{110}$ |
|---|---|---|---|---|---|---|---|
| 51 |  | 149–151° C | +174° | 0.61 | 0.66 | 0.51 | 0.61 |

*Determined in 0.5 N sodium bicarbonate solution.

The sulphonyl chloride $RCONHSO_2Cl$ used in Examples 49 – 51 is manufactured by heating a mixture of 40 mmols of carboxylic acid of the formula R—COOH, wherein R has the indicated meaning, in 120 ml of acetonitrile, with an equivalent amount of chlorosulphonylisocynate for 30 minutes to 80° C, then evaporating the mixture and dissolving the residue in 50 ml of acetonitrile.

The sulphonyl chloride R—$CONHSO_2Cl$ used in Examples 46 – 48 is manufactured by heating 40 mmols of sulphonamide of the formula R—H and 40 mmols of chlorosulphonylisocyanate in acetonitrile for 30 minutes to 80° C, evaporating the mixture and taking up the residue in 50 ml of acetonitrile.

What we claim is:

1. A compound of the formula

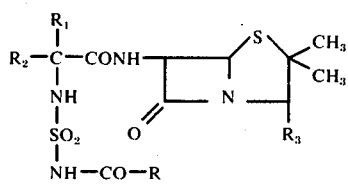

wherein $R_3$ denotes a free carboxy group, $R_1$ denotes hydrogen and $R_2$ denotes phenyl, thienyl or furyl or $R_1$ and $R_2$ together with the carbon atom form cycloalkyl having 4 to 7 carbon atoms and R represents hydrogen or a member selected from the group consisting of lower alkyl, lower alkyl mono- or disubstituted by lower alkoxy, lower alkanoyl, cyano, phenoxy, lower alkoxycarbonyl, halogen, or halogenphenoxy, phenyl, phenyl monosubstituted by di-lower alkylamino, lower alkanoylamino, carbamoyl, halogen, lower alkylsulphonamido, nitro, lower alkoxy or carboxy, naphthyl, phenyl-lower alkyl, pyridyl, pyridyl monosubstituted by lower alkyl, lower alkoxy, carbamoyl, di-lower alkylamino, lower alkanoylamino, lower alkoxycarbonyl hydroxy or halogen, furyl, thienyl, pyrrolyl, pyrazinyl, imidazolyl, or pyrimidinyl, lower alkoxy, alkoxy monosubstituted by lower alkoxy, di-lower alkylamino or mono- di- or trisubstituted by halogeno, phenyloxy, phenyloxy mono- or di-substituted by halogeno or di-lower alkylamino, naphthyloxy, phenylamino, N-lower alkyanoylphenylamino, morpholino, methanesulphonylamino, benzenesulphonylamino, benzenesulphonylamino monosubstituted by lower alkyl or halogen or naphthalenesulphonylamino, or a therapeutically useable ester or salt thereof.

2. A compound as claimed in claim 1, wherein $R_1$ represents hydrogen and $R_2$ represents phenyl, thienyl-(2) or furyl-(2), or a therapeutically usable ester or salt thereof.

3. A compound as claimed in claim 1, wherein $R_1$ represents hydrogen and $R_2$ represents phenyl and R denotes a lower alkyl group or a lower alkyl group monosubstituted or disubstituted by lower alkoxy, lower alkoxycarbonyl, lower alkanoyl, haloge or nitrile.

4. A compound as claimed in claim 1, wherein $R_1$ represents hydrogen and $R_2$ represents phenyl and R denotes a phenyl or naphthyl group, or a phenyl group which is substituted by halogen, carbamoyl, lower alkanoylamino or di-lower alkylamino.

5. A compound as claimed in claim 1, wherein $R_1$ represents hydrogen and $R_2$ represents phenyl and R denotes a pyrrolyl, pyrazinyl, pyrimidinyl, imidazolyl, pyridyl or pyridyl substituted by lower alkyl, lower alkoxy, halogen, methoxycarbonyl, carbamoyl, di-lower alkylamino, lower alkanoylamino or hydroxy.

6. A compound as claimed in claim 1, wherein $R_1$ represents hydrogen and $R_2$ represents phenyl and R denotes a furyl or thienyl.

7. A compound as claimed in claim 1, wherein $R_1$ represents hydrogen and $R_2$ represents phenyl and R denotes a lower alkoxy or phenoxy radical or such radical substituted by halogen or di-lower alkylamino.

8. Compounds as claimed in claim 1, wherein $R_1$ represents hydrogen and $R_2$ represents phenyl and R denotes an amino group which is substituted by an acyl group derived from a carboxylic acid or sulphonic acid.

9. A compound as claimed in claim 1, which is 6-[D-α-(pyridyl-carbonylsulphamylamino)-phenyl-acetamido]-penicillanic acid or a therapeutically usable salt thereof.

10. A compound as claimed in claim 1, which is 6-[D-α-(toluenesulphonylcarbamoylsulphamylamino)-phenyl-acetamido penicillanic acid or a therapeutically usable salt thereof.

11. A compound as claimed in claim 1, which is 6-[D-α-(naphthalenesulphonylcarbamoylsulphamylamino)-phenylacetamido]-penicillanic acid or a therapeutically usable salt thereof.

12. A compound as claimed in claim 1, which is 6-[D-α-(chlornicotinoylsulphamylamino)-phenylacetamido]-penicillanic acid or a therapeutically usable salt thereof.

* * * * *